United States Patent [19]

Yoshinaga et al.

[11] 3,978,228
[45] Aug. 31, 1976

[54] METHOD FOR KILLING NOXIOUS FUNGI IN PLANTS USING DIHALO SULFONATES

[75] Inventors: Eiichi Yoshinaga, Fujieda; Shigeki Wakamori, Shimizu; Gosaburo Dowke, Tokyo; Kiyoshi Takita, Shimizu, all of Japan

[73] Assignee: Kumiai Chemical Industry Co., Ltd., Tokyo, Japan

[22] Filed: Mar. 24, 1975

[21] Appl. No.: 561,365

Related U.S. Application Data

[63] Continuation of Ser. No. 312,323, Dec. 5, 1972, abandoned.

[30] Foreign Application Priority Data

Dec. 13, 1971  Japan............................. 46-100843

[52] U.S. Cl.................................... 424/303; 71/103
[51] Int. Cl.$^2$........................................... A01N 9/14
[58] Field of Search.......... 424/303; 260/456, 456 P

[56] References Cited
UNITED STATES PATENTS

| | | | |
|---|---|---|---|
| 2,474,350 | 6/1949 | Eilerman..................... | 260/456 R X |
| 2,689,862 | 9/1954 | Knowles......................... | 260/456 P |
| 2,921,944 | 1/1960 | Buecheler et al. .......... | 260/456 R X |
| 3,228,827 | 1/1966 | Larson et al....................... | 424/303 |
| 3,332,976 | 7/1967 | Freedman....................... | 424/303 X |
| 3,346,613 | 10/1967 | Larson et al..................... | 424/303 X |
| 3,395,231 | 7/1968 | White ................................. | 424/303 |
| 3,395,232 | 7/1968 | White ................................. | 424/303 |
| 3,818,102 | 6/1974 | Partos............................... | 424/303 |

FOREIGN PATENTS OR APPLICATIONS

| | | |
|---|---|---|
| 1,205,338 | 11/1965 | Germany |
| 4,210,377 | 6/1967 | Japan |
| 1,079,400 | 8/1967 | United Kingdom |

OTHER PUBLICATIONS

J. of Org. Chem. of the USSR, 1971, pp. 345–349.

*Primary Examiner*—James O. Thomas, Jr.
*Assistant Examiner*—Allen J. Robinson
*Attorney, Agent, or Firm*—Stevens, Davis, Miller & Mosher

[57] ABSTRACT

Noxious fungi on plants are controlled by applying thereto compounds having the general formula

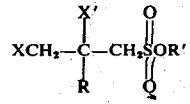

wherein X and X' are halogen atoms, R is hydrogen atom or methyl group and R' is alkyl, haloalkyl, phenyl group or phenyl group substituted with at least one of halogen atom, alkyl group, alkoxy group and nitro group.

2 Claims, No Drawings

METHOD FOR KILLING NOXIOUS FUNGI IN PLANTS USING DIHALO SULFONATES

This is a continuation, of application Ser. No. 312,323, filed Dec. 5, 1972 now abandoned.

The present invention relates to compositions for killing noxious organisms containing compounds having the general formula

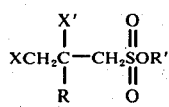

wherein X and X' are halogen atoms, R is hydrogen atom or methyl group and R' is alkyl, haloalkyl, phenyl group or phenyl group substituted with at least one of halogen, alkyl, alkoxy and nitro groups, as an active ingredient and further to a process for using said compounds, the novel compounds as shown by the general formula and a process for producing said compounds.

The inventors have made various investigations with respect to the sulfonates having the above described formula and found that these compounds are very active as soil sterilizing composition, fungicide, seed sterilizing composition, slime controlling composition, miticide, insecticide and herbicide. Particularly, when these compounds are used as the soil sterilizing composition, they are very active against disease due to Pellicularia genus, such as damping-off due to *Pellicularia filamentosa* and disease due to Fusarium genus, such as Fusarium wilt due to *Fusarium oxysporum*. When these compounds are used as fungicide, they are active preventively and therapeutically against rice blast (*Piricularia oryzao*), sheath bright (*Pellicularia sasakii*) and canker of oranges (*Xanthomonas citri*). Furthermore, these compounds are very active against Bakanae disease (*Gibberella fugikuroi*) by sterilizing seeds. Moreover, these compounds are useful as a slime controlling agent and for example, these compounds are active against bacteria, such as *Aerobacter aerogenus*, *Bacillus subtilis*, *Pseudomonas aeroginosa*, etc. and fungi, such as *Aspergillus niger*, *Penicillium steckii*, *Rhizopus nigricans* and the like.

In addition, these compounds are very active as miticides by spraying on leaves or roots against mites infected on vegetables, such as cucumber, egg-plant, tomato and the like, fruit-trees such as orange, apple, pear, etc. and flowers, such as chrysanthemum, rose, tulip. Further, these compounds are active against very harmful insects in the rice plant cultivation, such as rice stem borer, plant hopper, leaf hopper, cabbage armyworm, aphid and the like. Moreover, these compounds may be used as pesticides for animals, such as fishes, poutries and the like.

The compounds having the above described general formula and to be used in the present invention are produced by the following methods.

An alkenesulfonate having the general formula

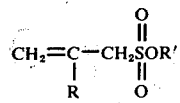

wherein R and R' have the same meanings as described above, is dissolved in an inert solvent, such as carbon tetrachloride and the like and then reacted with a halogen at a temperature of 10°–20°C in an amount of halogen of 10–20% excess based on the molar ratio.

Alternatively, a dihalogenosulfonic acid halide having the general formula

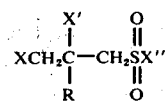

wherein X, X' and R have the same meanings as described above and X'' is a halogen atom, is reacted with an alcohol or phenol having the general formula

wherein R' has the same meanings as described above, in the presence of a hydrogen halide acceptor, such as sodium hydroxide, pyridine and the like.

The production process will be explained by the following examples.

Compound 1

Methyl 2,3-dichloropropanesulfonate

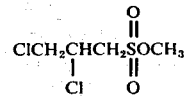

To a solution of 13.6 g of methyl 2-propenesulfonate in 80 ml of chloroform was added 7.1 g of chlorine absorbed in 20 ml of chloroform dropwise with stirring below 0°C. After the addition, the mixture was stirred for two hours at room temperature. By distillation of the solvent and fractionation, 14.5 g of methyl 2,3-dichloropropanesulfonate, B.P. 89°–92°C/0.5 mmHg, was obtained in a yield of 70.0%.

Compound 2

2,2,2-Trichloroethyl 2,3-dichloropropanesulfonate

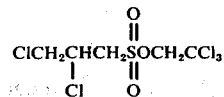

B.P. 131°–134°C/0.05 mmHg.

Compound 3

Phenyl 2,3-dichloropropanesulfonate

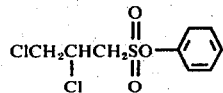

To a solution of 11.9 g of phenyl 2-propenesulfonate in 80 ml of chloroform was added 7.1 g of chlorine absorbed in 20 ml of chloroform dropwise with stirring below 0°C. After the addition, the mixture was stirred for two hours at room temperature. By distillation of the solvent and fractionation, 22.4 g of phenyl 2,3-dichloropropanesulfonate, B.P. 120°–125°C/0.005 mmHg, was obtained in a yield of 83.3%.

Compound 4

4-Cresyl 2,3-dichloropropanesulfonate

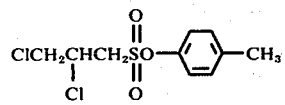

B.P. 145°–149°C/0.015 mmHg

Compound 5

4-Chlorophenyl 2,3-dichloropropanesulfonate

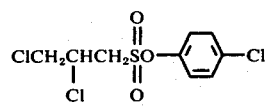

To a solution of 23.2 g of 4-chlorophenyl 2-propenesulfonate in 80 ml of chloroform was added 7.1 g of chlorine absorbed in 20 ml of chloroform dropwise with stirring below 0°C. After the addition, the mixture was stirred for two hours at room temperature. By distillation of the solvent and fractionation, 25.5 g of 4-chlorophenyl 2,3-dichloropropanesulfonate, B.P. 143°–145°C/0.015 mmHg, was obtained in a yield of 84.2%.

Compound 6

2,4-Dichlorophenyl 2,3-dichloropropanesulfonate

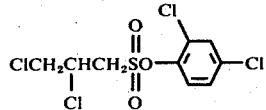

B.P. 150°–155°C/0.01 mmHg

Compound 7

4-Bromophenyl 2,3-dichloropropanesulfonate

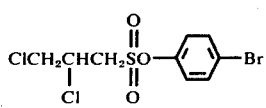

B.P. 164°–166°C/0.025 mmHg

Compound 8

2-Nitrophenyl 2,3-dichloropropanesulfonate

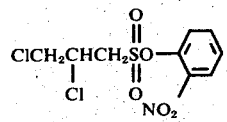

To a solution of 24.3 g of 2-nitrophenyl 2-propenesulfonate in 80 ml of chloroform was added 7.1 g of chlorine absorbed in 20 ml of chloroform dropwise with stirring below 0°C. After the addition, the mixture was stirred for two hours at room temperature. By distillation of the solvent and fractionation, 25.2 g of 2-nitrophenyl 2,3-dichloropropanesulfonate, B.P. 167°–169°C/0.015 mmHg, was obtained in a yield of 80.3%.

Compound 9

4-Cresyl 2,3-dibromopropanesulfonate

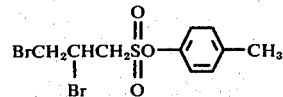

To a solution of 21.2 g of 4-cresyl 2-propenesulfonate in 80 ml of chloroform was added 16.0 g of bromine in 20 ml of chloroform dropwise with stirring below 0°C. After the addition, the mixture was stirred for two hours at room temperature. By distillation of the solvent and fractionation, 34.8 g of 4-cresyl 2,3-dibromopropanesulfonate, B.P. 159°–162°C/0.02 mmHg, was obtained in a yield of 93.5%.

Compound 10

4-Methoxyphenyl 2,3-dibromopropanesulfonate

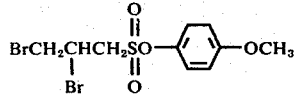

To a solution of 22.8 g of 4-methoxyphenyl 2-propenesulfonate in 80 ml of chloroform was added 16.0 g of bromine in 20 ml of chloroform dropwise with stirring below 0°C. After the addition, the mixture was stirred for two hours at room temperature. By distillation of the solvent and fractionation, 32.2 g of 4-methoxyphenyl 2,3-dibromopropanesulfonate, B.P. 176°–182°C/0.015 mmHg, was obtained in a yield of 82.9%.

Compound 11

4-Chlorophenyl 2,3-dibromopropanesulfonate

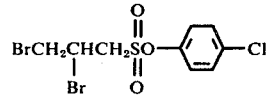

To a solution of 23.3 g of 4-chlorophenyl 2-propene-sulfonate in 80 ml of chloroform was added 16.0 g of bromine in 20 ml of chloroform dropwise with stirring below 0°C. After the addition, the mixture was stirred for two hours at room temperature. By distillation of the solvent and fractionation, 33.0 g of 4-chlorophenyl 2,3-dibromopropanesulfonate, B.P. 158°–162°C/0.008 mmHg, was obtained in a yield of 84.1%.

Compound 12

2-Nitrophenyl 2,3-dibromopropanesulfonate

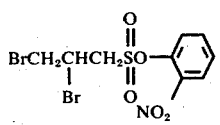

To a solution of 24.3 g of 2-nitrophenyl 2-propene-sulfonate in 80 ml of chloroform was added 16.0 g of bromine in 20 ml of chloroform dropwise with stirring below 0°C. After the addition, the mixture was stirred for two hours at room temperature. By distillation of the solvent and fractionation, 26.2 g of 2-nitrophenyl 2,3-dibromopropanesulfonate, B.P. >180°C/0.02 mmHg. $n_D^{20}$ 1.5721, was obtained in a yield of 65.0%.

Compound 13 n-Propyl 2,3-dibromo-2-methylpropanesulfonate

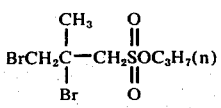

To a solution of 17.8 g of n-propyl 2-methyl-2-propenesulfonate in 80 ml of chloroform was added 16.0 g of bromine in 20 ml of chloroform dropwise with stirring below 0°C. After the addition, the mixture was stirred for two hours at room temperature. By distillation of the solvent and fractionation, 26.7 g of n-propyl 2,3-dibromo-2-methylpropanesulfonate, B.P. 109°–115°C/0.01 mmHg, was obtained in a yield of 79.0%.

Compound 14 n-Octyl 2,3-dibromo-2-methylpropanesulfonate

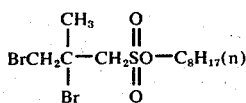

To a solution of 24.8 g of n-octyl 2-methyl-2-propenesulfonate in 80 ml of chloroform was added 16.0 g of bromine in 20 ml of chloroform dropwise with stirring below 0°C. After the addition, the mixture was stirred for two hours at room temperature. By distillation of the solvent and fractionation, 28.2 g of n-octyl 2,3-dibromo-2-methylpropanesulfonate, B.P. 162°–164°C/0.02 mmHg, was obtained in a yield of 69.1%.

Compound 15

2,3-Dibromopropyl 2,3-dibromo-2-methylpropanesulfonate

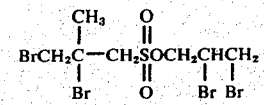

To a solution of 17.6 g of allyl 2-methyl-2-propenesulfonate in 80 ml of chloroform was added 32.0 g of bromine in 20 ml of chloroform dropwise with stirring below 0°C. After the addition, the mixture was stirred for two hours at room temperature. By distillation of the solvent and fractionation, 26.6 g of 2,3-dibromopropyl 2,3-dibromo-2-methylpropanesulfonate, B.P. 181°–182°C/0.005 mmHg, was obtained in a yield of 53.6%.

Compound 16

Phenyl 2,3,-dibromo-2-methylpropanesulfonate

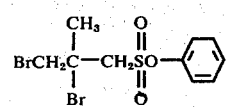

To a solution of 20.9 of phenyl 2-methyl-2-propenesulfonate in 80 ml of chloroform was added 16.0 g of bromine in 20 ml of chloroform dropwise with stirring below 0°C. After the addition, the mixture was stirred for two hours at room temperature. By distillation of the solvent and fractionation, 27.1 g of phenyl 2,3-dibromo-2-methylpropanesulfonate, B.P. 130°–135°C/0.01 mmHg, was obtained in a yield of 72.8%.

Compound 17

3-tert-Butylphenyl 2,3-dibromo-2-methylpropanesulfonate

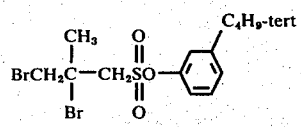

To a solution of 26.8 g of 3-tert-butylphenyl 2-methyl-2-propenesulfonate in 80 ml of chloroform was added 16.0 g of bromine in 20 ml of chloroform dropwise with stirring below 0°C. After the addition, the mixture was stirred for two hours at room temperature. By distillation of the solvent and fractionation, 40.4 g of 3-tert-butylphenyl 2,3-dibromo-2-methylpropanesulfonate, B.P. 158°–160°C/0.008 mmHg, was obtained in a yield of 94.4%.

Compound 18

2,6-Dichlorophenyl 2,3-dibromo-2-methylpropanesulfonate

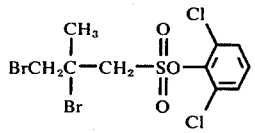

To a solution of 28.1 g of 2,6-dichlorophenyl-2-methyl-2-propenesulfonate in 80 ml of chloroform was added 16.0 g of bromine in 20 ml of chloroform dropwise with stirring below 0°C. After the addition, the mixture was stirred for two hours at room temperature. By distillation of the solvent, 30.1 g of 2,6-dichlorophenyl 2,3-dibromo-2-methylpropanesulfonate, M.P. 74°–76°C, was obtained in a yield of 68.3%.

Compound 19

4-Nitrophenyl 2,3-dibromo-2-methylpropanesulfonate

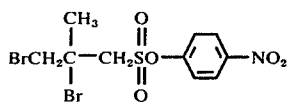

To a solution of 25.7 g of 4-nitrophenyl 2-methyl-2-propenesulfonate in 80 ml of chloroform was added 16.0 g of bromine in 20 ml of chloroform dropwise with stirring below 0°C. After the addition, the mixture was stirred for two hours at room temperature. By distillation of the solvent, 29.9 g of 4-nitrophenyl 2,3-dibromo-2-methylpropanesulfonate, M.P. 56°–58°C, was obtained in a yield of 71.7%.

The above described compounds are used together with ordinarily used inert carriers. The carriers may be solid or liquid. The compounds are mixed with inert carriers, and if necessary, with surfactants as a dispersant or a wetting agent, and used in the form of a dust, a wettable powder, an emulsifiable concentrate or a granule. The solid carrier includes talc, clay, kaolin, diatomaceous earth, white carbon, polyvinyl alcohol, sawdust, urea, ammonium sulfate, etc.

The liquid carrier includes ordinarily used solvents, for example, water, aliphatic compounds, such as acetone, acetonitrile, methyl sulfoxide, etc., and aromatic compounds such as toluene, xylene, methylnaphthalene, etc.

The compounds of the present invention are used, for example, in the following way.

1. The compound is mixed with a solid carrier to prepare a dust.
2. The compound is mixed with a solid carrier, 1 to 3% by weight of a wetting agent, such as alkylarylsulfonate, polyoxyethylenealkylaryl ether, laurylsulfate or polyoxyethylenealkylarylsulfonate, and 1 to 3% by weight of a dispersing agent, such as ligninsulfonate, PVA, CMC or a condensate of alkylarylsulfonate with formaldehyde to prepare a wettable powder, which is diluted with water to a proper concentration and used.
3. The compound is mixed with an organic solvent, and 5 to 15% by weight of an emulsifier, such as polyoxyethylenealkylaryl ether, polyoxyethylenealkyl ether, polyoxyethylene fatty acid ester, alkylarylsulfonate, polyoxyethylenepolyalkyldiphenyl ether, to prepare an emulsifiable concentrate, which is diluted with water to a proper concentration and used.
4. The compound is mixed with a solid carrier, a surfactant and other additives to prepare a granule.

The compounds of the present invention can kill and prevent safely various noxious bacteria, noxious insects, mites, noxious fungi and weeds without phytotoxicity in a low concentration.

Moreover, the compounds of the present invention can be added to feeds as a bactericide for animal.

The present invention will be illustrated in more detail by the following examples and experiments. The additives and active ingredients can be varied within a wide range without departing from the spirit and scope of the present invention.

EXAMPLE 1

Dusts

A mixture of 10 parts by weight (hereinafter, part means by weight) of the compound 1 as described above, 1 part of white carbon, 40 parts of talc and 49 parts of kaolin was blended and pulverized into fine powders.

EXAMPLE 2

Wettable powder

A mixture of 50 parts of the compound 5 as described above, 2 parts of sodium dodecylsulfate, 3 parts of sodium dinaphthylmethanesulfonate, 5 parts of white carbon and 40 parts of diatomaceous earth was blended homogeneously and pulverized into a wettable powder.

EXAMPLE 3

Emulsifiable concentrate

A mixture of 30 parts of the compound 10 as described above, 15 parts of dimethylformamide, 35 parts of cyclohexanone and 20 parts of a mixture of polyoxyethylenenonylphenyl ether and potassium benzenesulfonate was mixed homogeneously to form an emulsifiable concentrate.

EXAMPLE 4

Granule

A mixture of 20 parts of the compound 15 as described above, 20 parts of bentonite, 3 parts of sodium ligninsulfonate, 2 parts of sodium alkylbenzenesulfonate, 55 parts of talc and a small amount of water was blended to disperse the active ingredient uniformly, then granulated by means of a granulating machine and dried to obtain a granule.

An explanation will be made with respect to the activity against organisms of the above described compounds of the present invention.

EXPERIMENT 1

Test of anti-microbial spectrum

A wettable powder prepared from each of the compounds 1 to 19, according to Example 2, was diluted with water to prepare a dispersion containing 100 ppm of the compound.

Then, 1 ml of the dispersion was added to 9 ml of a potato culture medium, and the mass was stirred homogeneously and poured into a Petri dish. Microorganisms to be tested, which had been grown up in another potato culture medium, were punched out in a diameter of 9 mm, and added to the above described Petri dishes. 24 hours after the addition, the growth degree of the microorganisms was determined. In the test of *Mycoplasma gallisepticum* 2.7 ml of the cultivated solution, in which the bacteria to be tested is incubated in a liquid culture, was put into a test tube and to the test tube was added 0.3 ml of the above described diluted dispersion of the compound, and the determination was effected 4 days after the addition.

In the above test, the following microorganisms were used.

No. 1 : *Aeromonas liquefasciens* of eel
No. 2 : *Mycoplasma gallisepticum* of chickens
No. 3 : *Aerobacter aerogenes*
No. 4 : *Bacillus subtilis*
No. 5 : *Pseudomonas aeroginosa*
No. 6 : *Aspergillus niger*
No. 7 : *Penicillium steckii*
No. 8 : *Rhizopus nigricans*

The obtained results are shown in the following Table 1. In Table 1, the activity is shown by the following marks.

− : not grow at all
± : slightly grow
+ : grow similarly to non-treated case

Table 1

| Sample compound | | Microorganism and activity therefor | | | | | | |
|---|---|---|---|---|---|---|---|---|
| | | 1 | 2 | 3 | 4 | 5 | 6 | 7 | 8 |
| Compound | 1 | ± | − | − | − | − | − | − | − |
| " | 2 | − | − | − | − | − | − | − | − |
| " | 3 | − | − | − | − | − | − | − | − |
| " | 4 | − | − | − | − | − | − | − | − |
| " | 5 | − | − | − | − | − | − | − | − |
| " | 6 | − | − | − | − | − | − | − | − |
| " | 7 | − | − | − | − | − | − | − | − |
| " | 8 | − | − | − | − | − | − | − | − |
| " | 9 | − | − | − | − | − | − | − | − |
| " | 10 | − | − | − | − | − | − | − | − |
| " | 11 | − | − | − | − | − | − | − | − |
| " | 12 | − | − | − | − | − | − | − | − |
| " | 13 | − | − | − | ± | − | − | − | ± |
| " | 14 | − | − | − | − | − | − | − | − |
| " | 15 | − | − | − | − | − | − | − | − |
| " | 16 | − | − | − | − | − | ± | − | − |
| " | 17 | − | − | − | − | − | − | − | − |
| " | 18 | − | − | − | − | − | − | − | − |
| " | 19 | − | − | − | − | − | − | − | − |
| Non-treated | | + | + | + | | + | + | + | + |

EXPERIMENT 2

Test for preventing Bakanae disease of rice plant by sterilizing seedrices

Seedrices naturally infected with Bakanae disease (rice species: Sasanishiki) were immersed in the dispersion obtained by diluting each of the emulsifiable concentrates prepared following to Example 3 to the given concentration as shown in the following Table 2, for 18 hours and then washed with water and dried in air. For the immersing, 50 ml of the diluted dispersion was used per 10 g of the dried seedrices. 10 g of the dried seedrices were sown on a soil bed for growing the young plant for machine planting and the bed was placed in a box for growing young plant for 10 days and then left to stand in a greenhouse. 3 weeks after sown, the number of the young rice plants infected with *Gibberella fugikuroi* were determined to count the morbidity. The test was effected in 3 replications per one active ingredient and the test results are shown in the average value of the 3 replications in the following Table 2.

Table 2

| Sample compound | | Concentration (ppm) | Morbidity (%) | Phytotoxicity |
|---|---|---|---|---|
| Compound | 1 | 500 | 14.0 | no |
| " | 3 | " | 10.5 | " |
| " | 4 | " | 14.3 | " |
| " | 5 | " | 14.0 | " |
| " | 6 | " | 14.9 | " |
| " | 9 | " | 12.1 | " |
| " | 15 | " | 13.9 | " |
| " | 19 | " | 14.0 | " |
| Ruberon* (Comparative) | | 10 | 14.1 | " |
| Non-treated | | — | 54.2 | " |

Organic mercury agent: bis (ethylmercury) hydrogen phosphate.

EXPERIMENT 3

Fungicidal test against Fusarium wilt of cucumber

A bran culture medium containing *Fusarium oxysporium* of cucumber was mixed with soil sterilized in an autoclave in a ratio of 1:20. 100 g of sterilized soil was charged previously in an unglazed pottery pot having a diameter of 9 cm and then to the pot was charged 100 g of soil in which the above described soil infected with *Fusarium oxysporium* and each wettable powder prepared following to the above described Example 2 were mixed. Next day, 10 cucumber seeds were sown on the pot and the germination ratio and the sound young plant ratio were determined after 3 days. The test was effected in 3 replications per one active ingredient and the test results are shown in the following Table 3.

$$\text{Germination ratio} = \frac{\text{Number of germinated seeds}}{\text{Number of the total sown seeds}} \times 100$$

$$\text{Sound young plant ratio} = \frac{\text{Number of sound young plants}}{\text{Number of germinated seeds}} \times 100$$

Table 3

| Sample compound | | Dose (Kg/10α) | Germination ratio (%) | Sound young plant ratio (%) |
|---|---|---|---|---|
| Compound | 1 | 0.5 | 100 | 100 |
| " | 2 | " | 96.7 | 100 |
| " | 3 | " | 93.3 | 100 |
| " | 4 | " | 100 | 100 |
| " | 5 | " | 90.0 | 100 |
| " | 6 | " | 100 | 100 |
| " | 7 | " | 100 | 100 |
| " | 8 | " | 96.7 | 100 |
| " | 9 | " | 96.7 | 100 |
| " | 10 | " | 100 | 100 |
| " | 11 | " | 93.3 | 100 |
| " | 12 | " | 96.7 | 100 |
| " | 13 | " | 96.7 | 100 |
| " | 14 | " | 100 | 100 |
| " | 15 | " | 100 | 100 |

Table 3-continued

| Sample compound | Dose (Kg/10α) | Germination ratio (%) | Sound young plant ratio (%) |
|---|---|---|---|
| " 16 | " | 96.7 | 100 |
| " 17 | " | 90.0 | 100 |
| " 18 | " | 100 | 100 |
| " 19 | " | 100 | 100 |
| (Comparative agents) Phenyl 1,2-dichloro ethyl sulfonate* | " | 100 | 56.7 |
| Grand emulsifiable concentrate | Treated with 3,000 l of 1,000 times diluted solution | 83.3 | 80.0 |
| Non-treated soil containing fungi | — | 80.0 | 4.2 |
| Non-treated soil containing no fungi | — | 100 | 100 |

*Disclosed in German Patent No. 1,191,672.
Brand: 2,3-dibromopropionitrile 20%,
1,1,1-trichloro-2-nitroethane 20%.

EXPERIMENT 4

Fungicidal test against rice blast (Piricularia oryzae)

An unglazed pottery pot having a diameter of 9 cm, in which 20 young rice plants at 4–5 leaf-stage (Species: Aichiasahi) were planted, was mounted on a turn table and on the young rice plants was sprayed a dispersion of each wettable powder prepared following to Example 2 in which each wettable powder was diluted with water to the given concentration, under a spraying pressure of 0.5 Kg/cm² in an amount of 30 ml per pot. 3 days after the spraying, a dispersion of *Piricularia oryzae* spores which has been obtained by inoculating *Piricularia oryzae* successively on rice plant in a greenhouse and prepared so that 20 spores are contained in a field of vision of microscope (15×10 time), was sprayed on the young rice plants in a rate of 5 ml per pot. After the inoculation, the pot was placed in a wet house made of polyvinyl chloride film (saturation humidity, 24°C) for 24 hours and then transferred to a greenhouse, in which a high temperature was kept, whereby it was permitted to progress the disease spots. 7 days after the inoculation, the number of the disease spots with respect to 10 leaves per pot was determined and the preventing value was calculated. The test results are shown in the following Table 4.

$$\text{Preventing value} = \frac{\left[\begin{array}{c}\text{Number of disease}\\\text{spots in non-}\\\text{treated zone}\end{array}\right] - \left[\begin{array}{c}\text{Number of}\\\text{disease spots}\\\text{in treated zone}\end{array}\right]}{\left[\begin{array}{c}\text{Number of disease spots in}\\\text{non-treated zone}\end{array}\right]} \times 100$$

Table 4

| Sample compound | Concentration (ppm) | Preventing value (%) | Phyto-toxicity |
|---|---|---|---|
| Compound 2 | 500 | 98.3 | no |
| " 3 | " | 97.6 | " |
| " 5 | " | 96.4 | " |
| " 6 | " | 100 | " |
| " 10 | " | 100 | " |
| " 12 | " | 100 | " |
| " 14 | " | 90.8 | " |
| " 17 | " | 98.4 | " |
| " 18 | " | 100 | " |
| Blastin (Comparative agent) | " | 94.5 | " |
| Non-treated | — | 0 | " |

Blastin: Pentachlorobenzyl alcohol.

EXPERIMENT 5

Miticidal test against *Tetranichus telarius*

40–50 adults of *Tetranichus telarius* were infected on leaves of kidney bean young plant planted on a pot having a diameter of 12 cm in a greenhouse. Each wettable powder prepared following to Example 2 was diluted with water to 500 ppm of dispersion. In this dispersion was immersed the kidney bean young plant for 10 seconds and then the immersed young plant was left to stand in a greenhouse and 2 days after the treatment, the mortality was determined. The test results are shown in the following Table 5.

Table 5

| Sample compound | Mortality (%) |
|---|---|
| Compound 11 | 98.8 |
| " 12 | 99.8 |
| " 19 | 98.7 |
| Non-treated | 0 |

EXPERIMENT 6

Oricidal test against *Tetranichus telarius*

40–50 eggs of *Tetranichus telarius* were laid on leaves of kidney bean young plant planted in a pot having a diameter of 12 cm in a greenhouse. Each wettable powder prepared following to Example 2 was diluted with water to 500 ppm of dispersion. The thus treated kidney bean young plant was immersed in the resulting dispersion for 10 seconds and then left to stand in a greenhouse and 10 days after the treatment, the percentage for killing eggs was determined. The test results are shown in the following Table 6.

Table 6

| Sample compound | Eggs killing percentage (%) |
|---|---|
| Compound 4 | 86 |
| " 10 | 86.6 |
| " 16 | 100 |
| " 19 | 95 |

EXPERIMENT 7

Insecticidal test against plant hopper and leaf hopper

Into an icecream cup having a diameter of 5 cm containing previously germinated seedrices was charged 50 ml of 200 ppm of each dispersion of wettable powder prepared following to Example 2 and after the germinated seeds were immersed thoroughly in the dispersion, the water was discharged from the cup and 10 larvae of each green rice leaf hopper and small brown plant hopper were put in the cup. The test was made in 2 replications and the cup was kept in a thermostat at 25°C for 24 hours and the mortality was determined. The test results are shown in the following Table 7.

Table 7

| Sample compound | | Concentration (%) | Mortality (%) |
|---|---|---|---|
| Compound | 7 | 500 | 100 |
| " | 10 | " | 100 |
| " | 15 | " | 100 |
| Non-treated | | — | 0 |

EXPERIMENT 8

Insecticidal test against house fly

Powdery solid feed of bran and Ebios was added with each wettable powder prepared following to Example 2 and the mixture was thoroughly kneaded with such an amount of water that the concentration of the active ingredient is 2,000 ppm and then a pudding cup having a diameter of 8 cm was filled with the mixture. 10 adults of house fly were put in the cup and the cup was covered with a gauze and placed in a thermostat at 25°C and after 48 hours the mortality was determined. The test results are shown in the following Table 8.

Table 8

| Sample compound | | Mortality (%) |
|---|---|---|
| Compound | 1 | 100 |
| " | 2 | 100 |
| " | 6 | 96.7 |
| " | 11 | 100 |
| " | 13 | 100 |
| " | 14 | 100 |
| " | 18 | 100 |

Table 6-continued

| Sample compound | Eggs killing percentage (%) |
|---|---|
| Non-treated | 0 |

Table 8-continued

| Sample compound | Mortality (%) |
|---|---|
| Non-treated | 0 |

EXPERIMENT 9

Herbicidal test in flooded conditions

Soil was filled in a pot having 0.0002 are and in the surface layer of 1 cm was mixed soil containing seeds of pickerel-weed (*Monochoria vaginalis*) and the other broad leaf weeds [Toothcup, (*Rotala indica*), water wort (*Elatine triandra*) and red stem (*Ammonia multiflora*)] and then 20 seeds of barnyard grass (*Echinochloa Crus-galli*) were sown in the soil.

Each wettable powder prepared following to Example 2 was diluted with water and 2 days after the seeding, 3 ml of the resulting dispersion was added dropwise to the soil by a pipette. Thereafter, the soil in the pot was covered with water in a depth of 3 cm until the determination. After 2 weeks, the germination condition of the weeds was observed and the test results are shown in Table 9.

Table 9

| Sample compound | | Dose (Kg/10α) | Barnyard grass | Broad leaf weeds | Pickerel weed |
|---|---|---|---|---|---|
| Compound | 2 | 1.5 | × | × | × |
| " | 7 | " | × | × | +++ |
| " | 12 | " | × | × ~ +++ | +++ |
| " | 15 | " | × | +++ | × |
| " | 19 | " | +++ | +++ | +++ |
| Non-treated | | — | — | — | — |

| | | | |
|---|---|---|---|
| — | Germination percentage | | 100% |
| ± | " | | 80% |
| + | " | | 60% |
| ++ | " | | 40% |
| +++ | " | | 20% |
| × | Not germinate | | 0% |

What is claimed is:

1. A method for killing noxious fungi on plants, comprising
applying to noxious fungi on plants a fungicidally effective amount of a sulfonate having the formula

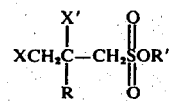

wherein X and X' are selected from the group consisting of bromine and chlorine, R is selected from the group consisting of hydrogen and methyl, and R' is selected from the group consisting of methyl, propyl, octyl, trichloroethyl, dibromopropyl, phenyl, monochlorophenyl, dichlorophenyl, monobromophenyl, nitro-phenyl, methyl-phenyl, butyl-phenyl and methoxy-phenyl.

2. A method for killing Fusarium diseases in plants comprising
applying to a Fusarium diseased area in plants having a Fusarium disease a Fusarium disease killing amount of a sulfonate having the formula

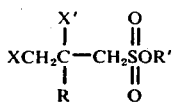

wherein X and X' are selected from the group consisting of bromine and chlorine, R is selected from the group consisting of hydrogen and methyl, and R' is selected from the group consisting of methyl, propyl, octyl, trichloroethyl, dibromopropyl, phenyl, monochlorophenyl, dichlorophenyl, monobromophenyl, nitro-phenyl, methyl-phenyl butyl-phenyl and methoxyphenyl.

* * * * *